US 8,126,231 B2

(12) United States Patent
Sakaida

(10) Patent No.: US 8,126,231 B2
(45) Date of Patent: Feb. 28, 2012

(54) MEDICAL IMAGE SEGMENTATION APPARATUS AND MEDICAL IMAGE SEGMENTATION PROGRAM

(75) Inventor: Hideyuki Sakaida, Minato-ku (JP)

(73) Assignee: Fujifilm Corporation, Tokyo (JP)

( * ) Notice: Subject to any disclaimer, the term of this patent is extended or adjusted under 35 U.S.C. 154(b) by 546 days.

(21) Appl. No.: 12/306,679

(22) PCT Filed: Jun. 22, 2007

(86) PCT No.: PCT/JP2007/062607
§ 371 (c)(1),
(2), (4) Date: Apr. 28, 2009

(87) PCT Pub. No.: WO2008/001694
PCT Pub. Date: Jan. 3, 2008

(65) Prior Publication Data
US 2010/0002917 A1    Jan. 7, 2010

(30) Foreign Application Priority Data
Jun. 29, 2006   (JP) .................................. 2006-180078

(51) Int. Cl.
*G06K 9/00* (2006.01)

(52) U.S. Cl. ......... 382/128; 382/131; 382/132; 382/173

(58) Field of Classification Search .................. 382/128, 382/131, 132, 173
See application file for complete search history.

(56) References Cited

U.S. PATENT DOCUMENTS
2009/0310835 A1*  12/2009  Kaus et al. .................. 382/128
2010/0128946 A1*   5/2010  Fidrich et al. .............. 382/131
2010/0268225 A1*  10/2010  Coe et al. ..................... 606/42

FOREIGN PATENT DOCUMENTS
JP   2003-116842 A   4/2003
JP   2005-110974 A   4/2005
JP   2005-137730 A   6/2005

OTHER PUBLICATIONS

Dejarnette Research, "CT Workflow in a PACS Environment", Internet <URL:http://www.dejarnette.com/Library/Article%20PDFs/CT%20Workflow%20in%20a%20PACS%20Environment.pdf>, Search on May 26, 2006, p. 1-18.

* cited by examiner

*Primary Examiner* — Marcos D. Pizarro
(74) *Attorney, Agent, or Firm* — Sughrue Mion, PLLC

(57) ABSTRACT

A medical image segmentation apparatus for segmenting one series obtained by continuous imaging of plural parts into plural series with respect to each part for easy interpretation of an image interpreter. The medical image segmentation apparatus includes an image segmenting unit for segmenting one series into a first series and a second series to thereby generate first image data representing the first series and second image data representing the second series, and a segmentation information adding unit for adding adjacent image information, which includes information for identification of the second series and information representing a positional relationship of the second series with the first series, to the first image data, and adding adjacent image information, which includes information for identification of the first series and information representing a positional relationship of the first series with the second series, to the second image data.

12 Claims, 10 Drawing Sheets

| AMOUNT OF AIR | 0~10% | 10~40% | 40~80% | 80~100% |
|---|---|---|---|---|
| HEAD | 0.9 | -1.0 | -1.0 | -1.0 |
| CHEST | -1.0 | 0.0 | 0.8 | 1.0 |
| ABDOMEN | -1.0 | 0.8 | -0.2 | -1.0 |
| LEG | 1.0 | -1.0 | -1.0 | -1.0 |

UPPER SECTION

▨ : HEAD
☐ : NECK
▩ : CHEST
☰ : ABDOMEN

LOWER SECTION

SLICE
NUMBER:

| 1 | 2 | 3 | 4 | 5 | 6 | 7 | 8 | 9 | 19 | 11 | 12 | 13 | 14 | 15 | PART |
|---|---|---|---|---|---|---|---|---|----|----|----|----|----|----|------|
| 0.0 | 0.0 | 0.7 | 0.3 | 0.8 | 0.2 | 0.6 | 0.7 | 0.9 | 1.3 | 1.5 | 2.1 | 1.6 | 1.4 | 1.8 | HEAD |
| 0.2 | 0.5 | 0.0 | 0.0 | 0.0 | 0.7 | 0.0 | 0.9 | 0.4 | 0.7 | 0.4 | 0.7 | 0.9 | 1.2 | 1.1 | NECK |
| 0.3 | 0.9 | 0.6 | 0.7 | 0.4 | 0.0 | 0.5 | 0.0 | 0.0 | 0.3 | 0.0 | 0.3 | 0.7 | 1.1 | 1.3 | CHEST |
| 1.0 | 1.4 | 1.1 | 1.7 | 1.3 | 0.6 | 0.9 | 0.3 | 0.7 | 0.0 | 0.2 | 0.0 | 0.0 | 0.0 | 0.0 | ABDOMEN |

SLICE
NUMBER:

| 1 | 2 | 3 | 4 | 5 | 6 | 7 | 8 | 9 | 19 | 11 | 12 | 13 | 14 | 15 | PART |
|---|---|---|---|---|---|---|---|---|----|----|----|----|----|----|------|
| 0.0 | 0.0 | 0.0 | 0.7 | 0.3 | 0.8 | 0.2 | 0.6 | 0.7 | 0.9 | 1.3 | 1.5 | 2.1 | 1.6 | 1.4 | HEAD |
| 0.0 | 0.5 | 0.0 | 0.0 | 0.7 | 1.0 | 0.8 | 1.1 | 1.0 | 1.4 | 1.3 | 2.0 | 2.4 | 3.3 | 2.7 | NECK |
| 0.2 | 0.9 | 1.1 | 0.7 | 0.4 | 0.7 | 1.5 | 0.8 | 1.1 | 1.3 | 1.4 | 1.6 | 2.7 | 3.5 | 4.6 | CHEST |
| 0.3 | 1.6 | 2.0 | 2.8 | 2.0 | 1.0 | 1.6 | 1.8 | 1.5 | 1.1 | 1.5 | 1.4 | 1.6 | 2.7 | 3.5 | ABDOMAN |

MEDICAL IMAGE SEGMENTATION APPARATUS AND MEDICAL IMAGE SEGMENTATION PROGRAM

CROSS REFERENCE TO RELATED APPLICATION

This application is a National Stage of International Application No. PCT/JP2007/062607 filed Jun. 22, 2007, claiming priority based on Japanese Patent Application No. 2006-180078, filed Jun. 29, 2006, the contents of all of which are incorporated herein by reference in their entirety.

TECHNICAL FIELD

The present invention relates to a medical image segmentation apparatus for generating image data representing axial images segmented with respect to each part based on image data acquired by a medical imaging modality and representing axial images showing plural parts, and a medical image segmentation program to be used in the apparatus.

BACKGROUND ART

Recent years, many medical images showing the interiors of living bodies have been used in medical diagnoses, and, in order to acquire such medical images, various technologies and apparatuses (modalities) such as X-ray imaging apparatus, X-ray CT (computed tomography) apparatus, ultrasonic (US) diagnostic apparatus, MRI (magnetic resonance imaging) apparatus, and PET (positron emission tomography) apparatus are widely used. Many of the apparatuses are digitalized, and diagnostic information processing systems within hospitals and so on are being constructed. Further, among the imaging technologies, CT and MRI have achieved significant results in detection and evaluation of lesion parts in living bodies because they can acquire and display axial images of a living body at relatively short intervals. Here, an axial image refers to a tomographic image that shows a surface perpendicular or substantially perpendicular to the body axis of an object to be inspected (so-called cross sectional surface). Hereinafter, the axial image is also simply referred to as "slice image".

At tomographic imaging for CT inspection or the like, not only one part (e.g., only the chest or abdomen) is necessarily imaged, but imaging is often sequentially performed over plural parts (e.g., from chest to abdomen, head to chest, or the like) in one inspection. Accordingly, usually, one series of slice images showing plural parts are segmented with respect to each part after imaging, and thereby, plural series are newly generated. Usually, a doctor (image interpretation doctor) acquires a series showing a part in charge and makes image interpretation.

As a related technology, DeJarnette Research Systems, Inc., "CT Workflow in a PACS Environment" (Internet <URL: http://www.dejarnette.com/Library/Article%20PDFs/CT%20Workflow%20in%20a%20PACS%20Environment.pdf>, searched on May 26, 2006) discloses an apparatus (Automatic Study Breakup Device) for receiving a worklist from a PACS (Picture Archiving and Communication System) or RIS (Radiology Information System), recognizing a set of processing to be integrated as one combined processing, sending it to a CT scanner to allow the scanner to perform a series of inspections, and breaking up thereby obtained images in association with individual processing and storing them in a PACS (pages 13-14).

However, series segmentation of segmenting one series of images of plural parts into plural series is not necessarily performed appropriately. For instance, when parts are erroneously recognized for the respective slice images, the images are segmented at incorrect slice positions. Further, when plural parts are shown in one slice image (e.g., a chest and an abdomen), if the slice image is included in one series (e.g., an abdomen series), in the other series (e.g., a chest series), a part is partially missed (e.g., the lower half of a lung field is not included in the chest series).

Even when the doctor during image interpretation notices the failure in series segmentation and the missing of parts, it is extremely difficult and takes a lot of efforts to search for associated series among an enormous amount of images to display the continuation of the series being interpreted. As a result, the image interpretation doctor becomes impossible to smoothly carry on the image interpretation.

DISCLOSURE OF THE INVENTION

Accordingly, in view of the above-mentioned points, an object of the present invention is to segment one series obtained by serial imaging of plural parts into plural series with respect to each part for easy interpretation by an image interpretation doctor.

In order to achieve the above-mentioned object, a medical image segmentation apparatus according to one aspect of the present invention is an apparatus for generating image data respectively representing plural series of images including at least first and second series of images based on image data representing one series of images including plural axial images, and the apparatus includes: image segmenting means for segmenting one series of images into a first series of images and a second series of images to thereby generate first image data representing the first series of images and second image data representing the second series of images; and segmentation information adding means for adding adjacent image information, which includes information for identification of the second series of images and information representing a positional relationship of the second series of images with the first series of images, to the first image data, and adding adjacent image information, which includes information for identification of the first series of images and information representing a positional relationship of the first series of images with the second series of images, to the second image data.

Further, a medical image segmentation program according to one aspect of the present invention is a program, embodied on a computer-readable medium, for generating image data respectively representing plural series of images including at least first and second series of images based on image data representing one series of images including plural axial images, and the program actuates a CPU to execute the procedures of: (a) segmenting one series of images into a first series of images and a second series of images to thereby generate first image data representing the first series of images and second image data representing the second series of images; and (b) adding adjacent image information, which includes information for identification of the second series of images and information representing a positional relationship of the second series of images with the first series of images, to the first image data, and adding adjacent image information, which includes information for identification of the first series of images and information representing a positional relationship of the first series of images with the second series of images, to the second image data.

In the present application, each axial image is also referred to as "slice image", and a set of axial images included in one series is referred to as "series of images".

According to the present invention, since information on the rest of the segmented series of images is added to image data representing plural series of images obtained by segmentation of one series of images, a series of images adjacent to the series of images currently being displayed can be easily searched for. Therefore, even when series segmentation is failed or there is a missing part in a series of images after segmentation, another series of images including the missing part can be easily searched for and displayed.

BEST MODE FOR CARRYING OUT THE INVENTION

Figure 1:
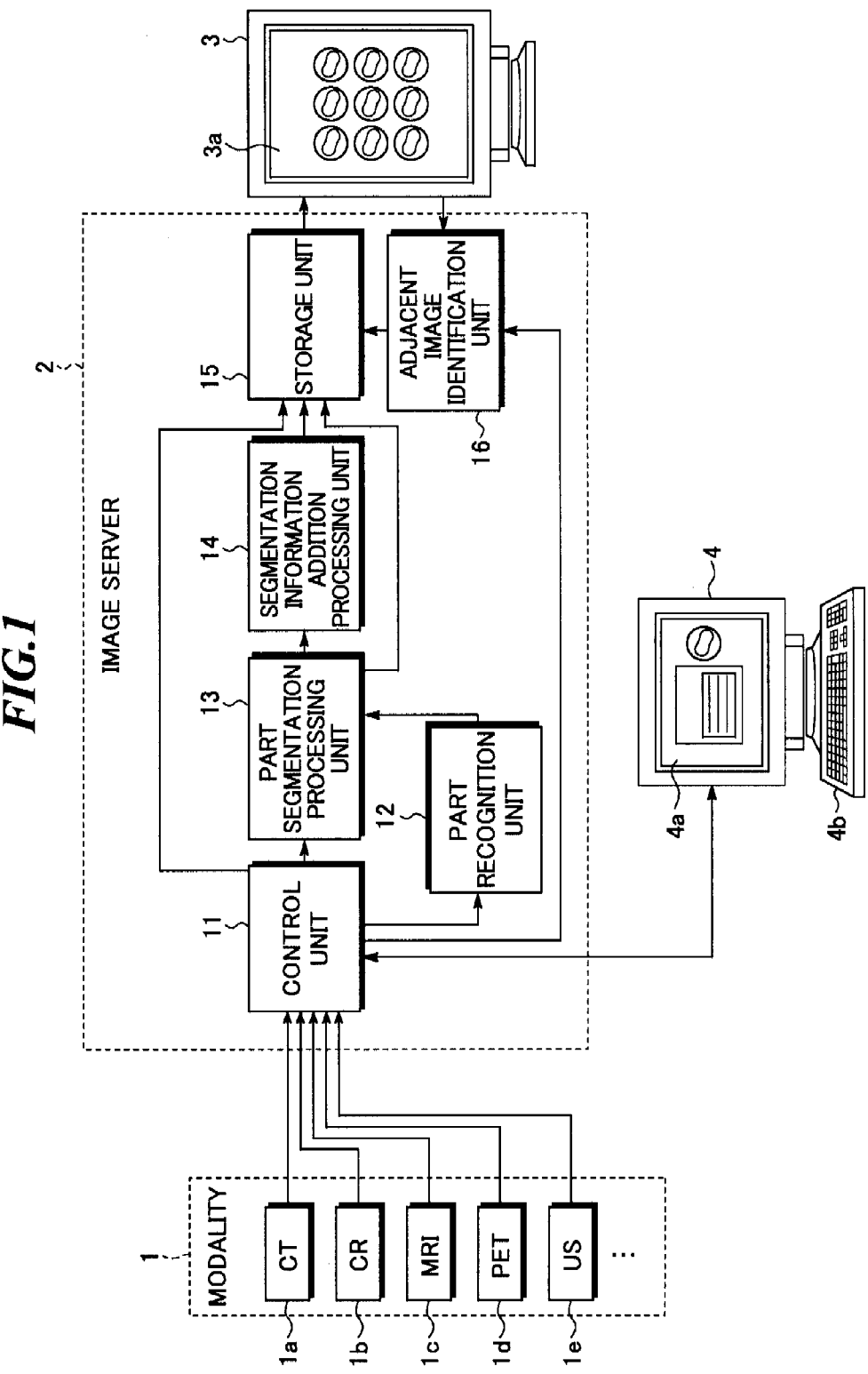
FIG. 1 shows a configuration of a medical image imaging system including a medical image segmentation apparatus according to the first embodiment of the present invention.

Hereinafter, some embodiments of the present invention will be explained in detail by referring to the drawings. The same reference numerals are assigned to the same component elements and the description thereof will be omitted.

FIG. 1 is a block diagram showing a configuration of a medical image imaging system including a medical image segmentation apparatus according to the first embodiment of the present invention. This medical image imaging system includes a modality 1 for performing imaging inspection of medical images on an object to be inspected, an image server 2, an image display terminal 3, and an image interpretation terminal 4. These devices 1-4 are compliant with the DICOM (Digital Imaging and Communications in Medicine) standard.

The modality 1 includes a medical image imaging apparatus such as a CT apparatus 1a, a CR (computed radiography) apparatus 1b, an MRI apparatus 1c, a PET apparatus 1d, and an ultrasonic diagnostic apparatus (US) 1e, and soon. These modalities 1a-1e generate image data by performing imaging inspection and output the data with image supplementary information to the image server 2.

The image server 2 is a PACS (Picture Archiving and Communication System) server for storing and managing image data acquired by the modality 1. The image server 2 has a medical image part segmentation function and operates not only as a typical image server (for storing image data and so on) but also as a medical image segmentation apparatus. The image server 2 outputs image data to the image display terminal 3 according to the request of the image interpretation terminal 4, which will be described later.

As shown in FIG. 1, the image server 2 has a control unit 11, a part recognition unit 12, a part segmentation processing unit 13, a segmentation information addition processing unit 14, a storage unit 15, and an adjacent image identification unit 16. The control unit 11 to the segmentation information addition processing unit 14 and the adjacent image identification unit 16 are configured by a CPU (central processing unit) and a medical image segmentation program according to the embodiment, for example.

The control unit 11 allows the storage unit 15 to store the image data outputted from the modality 1. Further, the control unit 11 confirms the orientation of the images (axial, coronal, sagittal, or the like) represented by the inputted image data, and also outputs the image data to the part recognition unit 12 when the orientation is axial. The orientation of images is acquired from image supplementary information provided with DICOM tag (0020, 0037): Image Orientation (Patient) or (0020, 0020): Patient Orientation.

The part recognition unit 12 recognizes which part of the object is shown in each axial image based on plural axial images (hereinafter, also referred to as "slice images") represented by one series of image data. Then, the unit generates information (part information) including recognition results (parts) and associates the information with the image data. The parts may be expressed by a character string of "Head", "Neck", "Chest", or the like, or expressed by an integral value that has been coded in advance of 1: head, 2: neck, 3: chest, or the like.

The part segmentation processing unit 13 recognizes boundaries between parts (slice locations where parts change) in the series based on the part information of the respective slice images generated by the part recognition unit 12, and sets segmentation locations of the series based on the boundaries. Then, by segmenting the series of images at the segmentation locations into plural series of images, image data respectively representing the plural series of images are generated. For example, when it is recognized that the 1st to 10th slices show the chest and that 11th and higher ordinal number slices show the abdomen in the series of images before segmentation, the region between the 10th slice and the 11th slice is recognized as a boundary between the chest and the abdomen, and image data representing the first series of images including the 1st to 10th slice images and image data representing the second series of images including the 11th and higher ordinal number slice images are generated.

The segmentation information addition processing unit 14 generates information in the following (1)-(3) (adjacent image information) and part information such as chest, abdomen, and so on ((0018, 0015): Body Part), and adds the information to the respective series after segmentation as image supplementary information.

(1) Information on Series Before Segmentation

The segmentation information addition processing unit 14 acquires image supplementary information (e.g., information to which DICOM tag (0028, 0030): Pixel Spacing has been added) common to series before segmentation and after segmentation from the image data representing the series of images before segmentation, for example, and adds the information to the image data of the respective series after segmentation.

(2) Information for Identifying Adjacent Series

The segmentation information addition processing unit 14 adds a file name or an identification code of the second series of images showing the abdomen, for example, to the image data of the first series of images showing the chest, and adds a file name or an identification code of the first series of images to the image data of the second series of images.

(3) Information Representing Positional Relationships Between Adjacent Series

For example, since the chest is at the "upper side" relative to the abdomen, the segmentation information addition processing unit 14 adds information representing "upper side" to the image data of the first series of images and adds information representing "lower side" to the image data of the second series of images. Alternatively, instead of the positional relationship between the series of images, positional coordinates of the respective series of images relative to a common coordinate system may be used as information representing the positional relationships with the adjacent series.

The operation of the part recognition unit 12 to the segmentation information addition processing unit 14 will be specifically explained later.

The storage unit 15 is, for example, a hard disk drive built in the image server 2, and stores image data before segmentation and image supplementary information thereof, image data after segmentation generated by the part segmentation processing unit 13, information added to the image data by the segmentation information addition processing unit 14, a control program for operating the respective units (medical image part segmentation program), and so on under control of the control unit 11. As the recording medium, not only the hard disk, but also an MO, an MT, a RAM, a CD-ROM, a DVD-ROM, or the like may be used. In this case, a drive unit for driving those recording media is built in the image server 2 or externally connected to the image server 2.

The segmentation information identification unit 16 searches for series of images as the rest of the segmented images of the series of images being displayed on the image display terminal 3 from image data stored in the storage unit 15, and causes the image display terminal 3 to display the rest of the segmented images, according to the command of the user (image interpretation doctor) inputted via the control unit 11 or the image display terminal 3. At searching, the information added to the image data representing the respective series of images by the segmentation information addition processing unit 14 is used.

The image display terminal 3 is a terminal device on which inspection images are displayed based on the externally inputted image data and has a high-definition display. Further, the image display terminal 3 may include an input device (e.g., an input button, keyboard, mouse, or the like) for the user to input commands. Plural axial images are schematically shown on a screen 3a of the image display terminal 3 shown in FIG. 1.

The image interpretation terminal 4 is a device to be used by the user (image interpretation doctor) for generating image interpretation reports and so on while referring to inspection images displayed on the image display terminal 3, and includes a screen 4a for displaying image interpretation reports, an input device 4b such as a keyboard, and so on.

Next, the configuration and operation of the part recognition unit 12 shown in FIG. 1 will be explained with reference to FIGS. 2-4.

Figure 2:
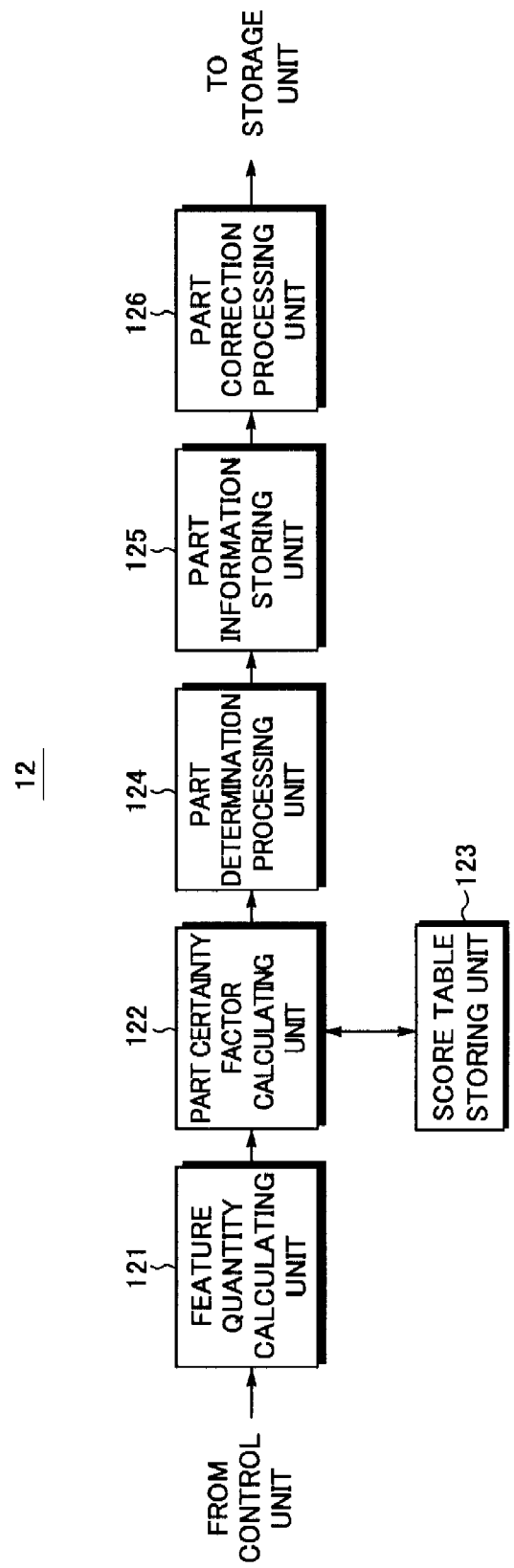
FIG. 2 is a block diagram showing functions of a part recognition unit shown in FIG. 1.

FIG. 2 is a block diagram showing functions of the part recognition unit 12 shown in FIG. 1. As shown in FIG. 2, the part recognition unit 12 includes a feature quantity calculating unit 121, a part certainty factor calculating unit 122, a score table storing unit 123, a part determination processing unit 124, a part information storing unit 125, and a part correction processing unit 126. Among the units, the feature quantity calculating unit 121 to the part determination processing unit 124 tentatively determine the parts shown in the respective slice images. Further, the part correction processing unit 126 corrects the part tentatively determined for the respective slice images based on part information of plural slice images. The part information of plural slice images will be explained as below.

Figure 3:
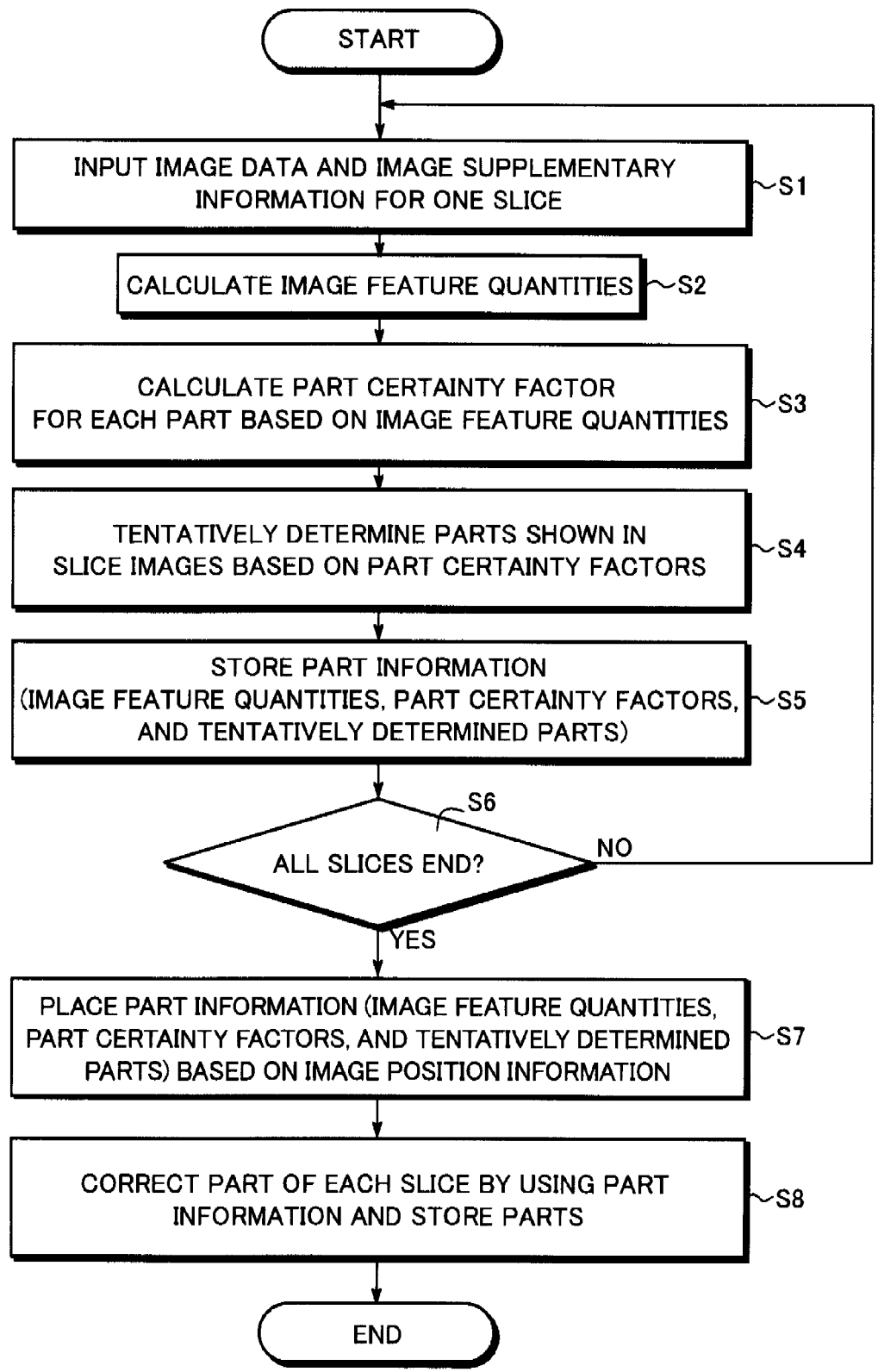
FIG. 3 is a flowchart showing an operation of the part recognition unit shown in FIG. 1.

FIG. 3 is a flowchart showing the operation of the part recognition unit 12. When the image data determined to represent axial images in the control unit 11 (FIG. 1) is inputted to the part recognition unit 12, the part recognition operation as described below is started.

At step S1, image data and the image supplementary information thereof are inputted for each slice to the feature quantity calculating unit 121. Here, the image supplementary information includes information representing image orientation ((0020, 0037): Image Orientation (Patient) or (0020, 0020): Patient Orientation), information representing the spacing of pixels ((0028, 0030): Pixel Spacing), information representing the thickness of a slice ((0018, 0050): Slice Thickness), information representing the number of pixels included in one row or column ((0028, 0010): Rows and (0028, 0011): Columns), information representing the three-dimensional coordinates in the upper left position of an image ((0020, 0032): Image position (Patient)) and so on. Here, the contents in the parentheses express DICOM tags and attribute names of the respective information.

At step S2, the feature quantity calculating unit 121 calculates a feature quantity for one slice image. Here, the feature quantity is numeral conversion of the feature of the body part shown by the slice image. The feature quantity is calculated based on the shape of the body part shown in the slice image as shown in the following (A), for example. Further, when the value of each pixel data (i.e., pixel brightness) corresponds to the body part property (tissue property or the like), the feature quantity may be calculated according to the value as shown in the following (B) and (C). For example, the value of pixel data in a CT image is determined by a CT value, and the CT value is a physical quantity representing the amount of radiation transmitted through the body. The CT value of water is 0 HU, the CT value in the air region is about −1000 HU, and the CT value in the bone region is about 250 HU to 3000 HU.

(A) Degree of Circularity of Entire Body Part

The degree of circularity "ρ" is calculated by the following equation (1) by using the area "S" of a target region and the length "L" around the region.

$$\rho = 4\pi S/L^2 \qquad (1)$$

The nearer a perfect circle the shape of the target region becomes, the closer to "1.0" the degree of circularity "ρ" becomes, and the farther from the perfect circle the shape becomes (e.g., the farther from "1" the ellipticity becomes), the smaller the degree becomes. For example, when the target region is the head, the degree of circularity is relatively high. Contrary, when the target region is the chest or abdomen, the degree of circularity is relatively low.

(B) Feature Quantity of Air Region: (Number of Pixels Having CT Values Representing Air Region)/(Number of Pixels of Entire Body Part)

For example, when the target region is the chest, the air region is relatively wide because of the existence of lungs. Contrary, when the target region is the head, the air region is nearly zero.

(C) Feature Quantity of Bone Region: (Number of Pixels Having CT Values Representing Bone Region)/(Number of Pixels of Entire Body Part)

For example, when the target region is the abdomen, the bone region relative to the entire body is a relatively small range. Contrary, when the target region is the leg, the bone region occupies the major part relative to the entire body.

Then, at step S3, the part certainty factor calculating unit 122 calculates a part certainty factor based on the feature quantity calculated by the feature quantity calculating unit 121. Here, the part certainty factor is numeric conversion of the likelihood that the target part is "certain part" (the likelihood of "head", the likelihood of "chest", or the like). In the embodiment, the part certainty factor is calculated by using a score table that has been prepared in advance.

Figures 4, 5:
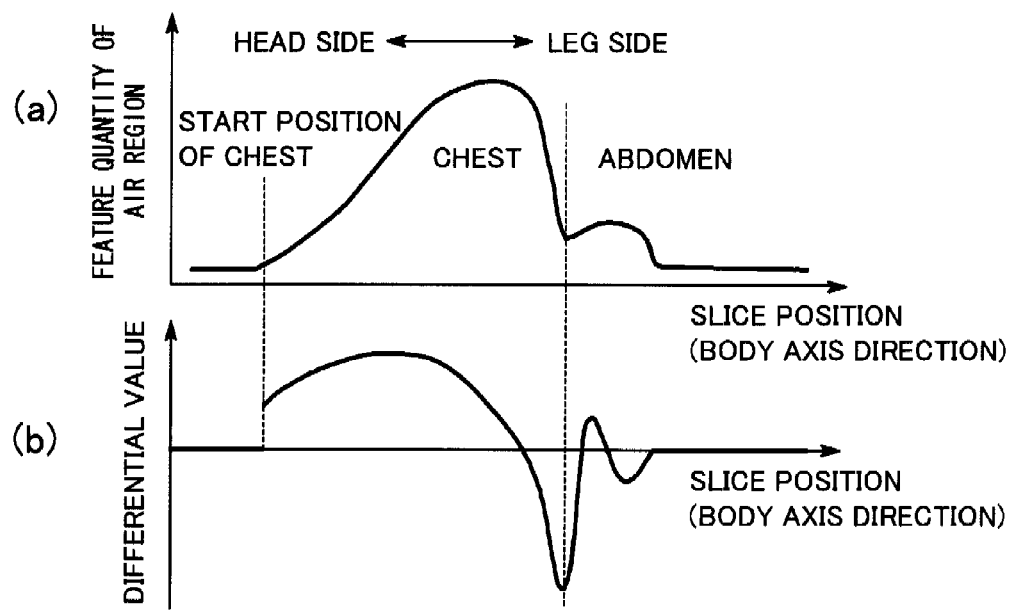
FIG. 4 shows a part certainty score table using feature quantities of air region.
FIG. 5 shows feature quantities of air region and differential values thereof.

FIG. 4 shows an example of score table to be used for calculation of part certainty factor. The score table is used when obtaining the likelihood of "head", the likelihood of "chest", the likelihood of "abdomen", and the likelihood of "leg" based on the value of the feature quantity of air region (the amount of air). In addition, "pelvis" may be used as a part item. Further, items (e.g., "head and neck part" or "chest and abdomen part") indicating the boundary between two adjacent parts (boundary region) or the region of a mixture of plural parts (mixture region, e.g., the head and neck or the chest and abdomen) may be used.

For example, when the feature quantity of air region of a body part shown in a CT image is 60%, by referring to the field of "40-80%" including 60% in the score table, it is found that the score of the likelihood of "head" of the body part is "−1.0", the score of the likelihood of "chest" is "0.8", the score of the likelihood of "abdomen" is "−0.2", and the score of the likelihood of "leg" is "−1.0".

Such a score table is created for each feature quantity and stored in the score table storing unit 123. The score table may be statistically created or intentionally created based on experiences of users (doctors or the like) or the like.

The part certainty factor calculating unit 122 obtains the scores of the likelihood of each "part" with respect to each feature quantity by referring to the score table, and sums up the scores for each part. Thus obtained sum of scores with respect to each part becomes the part certainty factor.

With reference to FIG. 3 again, at step S4, the part determination processing unit 124 tentatively determines the part having the largest value of the part certainty factors obtained at step S3 as the part of the body shown in the slice image. When there are plural parts with larger values and the difference between them is within a predetermined range (e.g., within 10%), both parts may be adopted. For example, the part certainty factors of the chest and the abdomen are larger, the part of the slice is determined to be "chest" or "abdomen".

Alternatively, when an item indicating a boundary region or a mixture region (e.g., "chest and abdomen part") is used, it may be adopted.

At step S5, the part information storing unit 125 stores the feature quantities obtained at step S2, the part certainty factors obtained at step S3, and the part tentatively determined at step S4 as part information (information on parts) of the slice images. All feature quantities are not necessarily stored, and only predetermined feature quantities (e.g., only the feature quantities obtained at step S8 described as below) may be stored.

The operation at steps S1-S5 is performed on all slice images included in one series (step S6).

When the part information on all slice images are obtained, at step S7, the part correction processing unit 126 places the part information stored in the part information storing unit 125 in the order of slices. This is because the image data generated in the modality (FIG. 1) is not necessarily sent to the image server 2 in the order of slices. The order of slices is determined based on the image position information (0020, 0032): Image position (Patient) of the image supplementary information. Alternatively, instead of step S7, the part information storing unit 125 may store the part information while placing them in the order of slices based on the image position information at step S5.

Then, at step S8, the part correction processing unit 126 corrects the parts tentatively determined for each slice by using part information of the plural slice images. The correction methods are the following (1)-(3), for example.

(1) Method Using Part Information of Adjacent Slices

This method is a method of correcting the part tentatively determined for a slice image based on the positional relationship with adjacent slices.

The case where the tentatively determined part is "neck" in the 1st to 5th slices, "head" in the 6th slice, "neck" in the 7th to 10th slices, "chest" in the 11th to 15th slices, "leg" in the 16th slice, "chest" in the 17th to 20th slices, and "abdomen" in the 121st to 30th slices will be considered. In this case, since the part is "neck" in the preceding and subsequent slices of the 6th slice, the determination that the 6th slice is "head" is a recognition error, and correctly "neck". Further, since the part is "chest" in the preceding and subsequent slices of the 16th slice, the determination that the 16th slice is "leg" is a recognition error, and correctly "chest". In this way, when the part tentatively determined for a slice image is different from the part in the preceding and subsequent slice images, the part of the slice image is corrected by referring to the preceding and subsequent slice images.

(2) Method Using Feature Quantities

This method is a method of correcting the part tentatively determined for a slice image based on the change in feature quantity in the body axis direction.

FIG. 5 (a) shows feature quantities of air region in the order of slice positions (in the body axis direction), and FIG. 5 (b) shows differential values of feature quantities of air region. As shown in FIG. 5 (b), from the observation of the change in feature quantity of air region from the upper section (head side) toward the lower section (leg side) of the object, it is found that there is a location where the feature quantity abruptly starts to increase. This location is set as the start position of the chest. Further, from the observation further toward the leg side, it is found that there is a location where the feature quantity changes from decrease to increase. The location is set as the boundary between the chest and the abdomen. When there is a slice image, which is tentatively determined as a part other than the chest, between the start position of the chest and the boundary between the chest and the abdomen, the part of the slice image is corrected to the chest.

(3) Method Utilizing Matching Curve

This method is a method of correcting the part tentatively determined for each slice image by referring to normal arrangement of parts in the object (e.g., human body).

Figure 6:
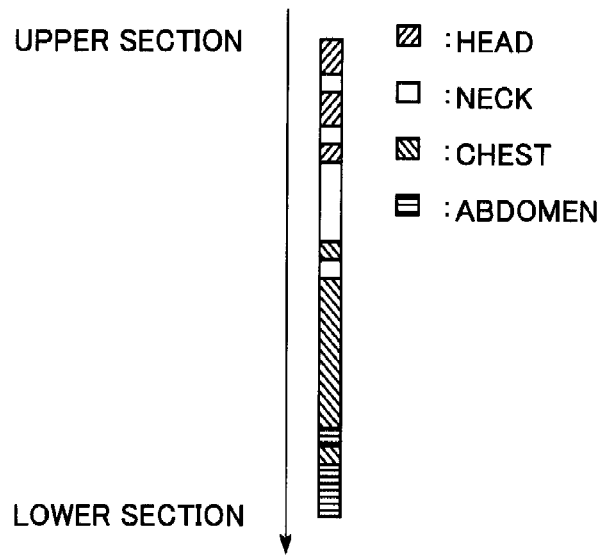
FIG. 6 is a diagram of tentatively determined parts (part recognition results) in the order of slices.

First, as shown in FIG. 6, the part tentatively determined for each slice image is placed in the order of slices from the upper section (head side) toward the lower section (leg side). As shown in FIG. 6, since the region where "Head" and "Neck" alternately appear and the region where "Neck" appears between "Chests" are seen in the part recognition result, it is considered that tentatively determined parts include many recognition errors.

Figure 7:
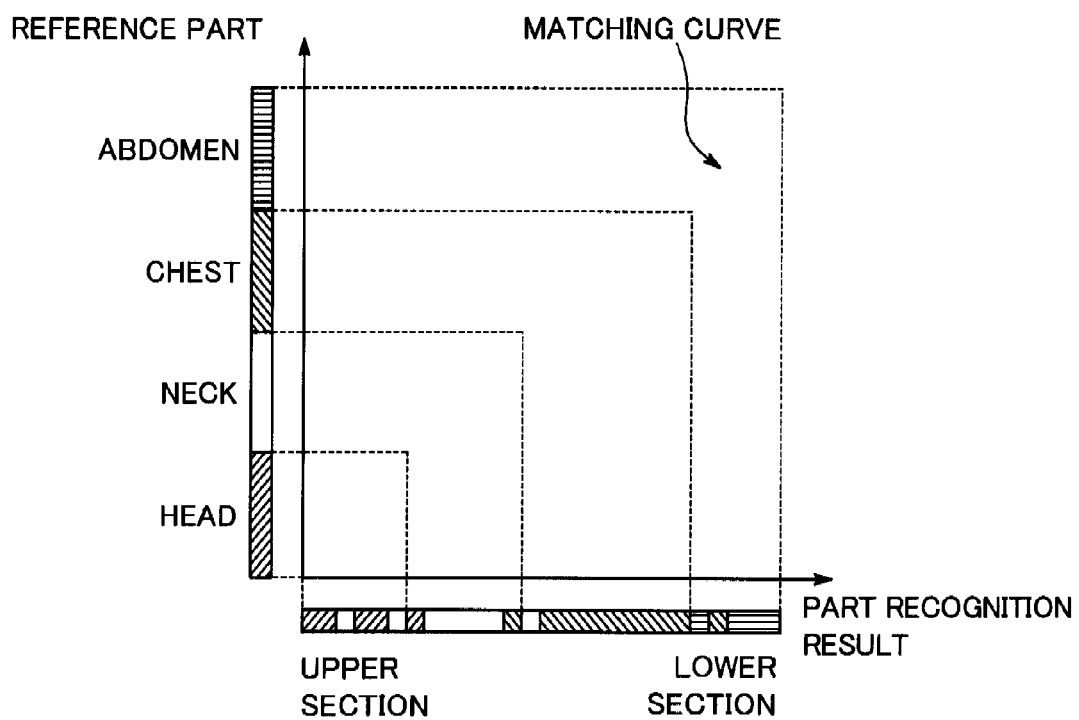
FIG. 7 shows a matching curve between the part recognition results and reference parts.

Then, as shown in FIG. 7, a matching curve between the part recognition results shown in FIG. 6 and the previously created reference parts is searched for. Here, since the parts of the human body are arranged in the order of head→neck→chest→abdomen, the reference parts arranged in such an order are created in advance as shown by the vertical axis in FIG. 7.

At the time of searching for the matching curve, given that the cost becomes higher when there is a mismatch between the part recognition result and the reference part, a curve that has the lowest cost is obtained. As a search method, various methods for solving the optimization problem are applicable. As below, a method of searching for a matching curve by using a dynamic programming method that is well known as one of the methods will be explained.

Figures 8, 9, 10:
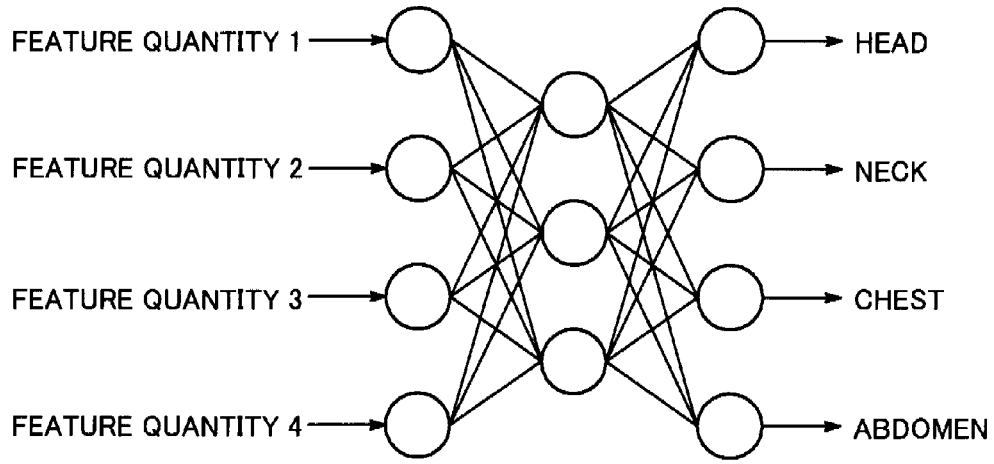
FIG. 8 is a weight map to be used for searching for a matching curve using a dynamic programming method.
FIG. 9 is a cost map used for searching for a matching curve using the dynamic programming method.
FIG. 10 is a diagram for explanation of a method of tentatively determining parts using the neural net.

First, a weight map as shown in FIG. 8 is created. In FIG. 8, the columns correspond to slice numbers and rows correspond to parts. In this weight map, the tentatively determined parts are set so that the weights are zero (areas enclosed by heavy lines). For example, with reference to FIG. 6, the first slice is tentatively determined as the head, and the value of the cell of the "Head" of the slice number "1" in the weight map is set to "0.0". Further, values of other cells are set larger than zero. Specifically, in the case where the certainty factor has been calculated for each slice image, the value of the difference between this certainty factor and the certainty factor of the tentatively determined part may be set, or a predetermined value other than the value may be set.

Then, a cost map as shown in FIG. 9 is created. In FIG. 9, the cost of each cell (n, m) is set as follows. Here, "n" indicates the slice number, and "m" indicates the part number (1: Head, 2: Neck, 3: Chest, 4: Abdomen).

(1, 1): Value of (1, 1) in weight map (see FIG. 8)
(n, 1): Value of (n−1, 1) in weight map+Predetermined value
(1, m): Value of (1, m−1) in weight map+Predetermined value
(n, m): Minimum value among the following (i)-(iii)
(i) Value of (n−1, m−1) in cost map+Value of (n, m) in weight map
(ii) Value of (n, m−1) in cost map+Value of (n, m) in weight map+Predetermined value
(iii) Value of (n−1, m) in cost map+Value of (n, m) in weight map+Predetermined value Then, the surrounding minimum values are sequentially traced from right to left on the cost map. Thereby, a correspondence map of slice numbers to parts is created.

As shown in FIG. 7, the correction of parts is performed by replacing the tentatively determined parts to corresponding parts in the reference parts based on the matching curve obtained as described above.

With reference to FIG. 3 again, at step S8, the part correction processing unit 126 outputs the corrected part information as image supplementary information to the storage unit 15 and allows the storage unit to store the information. The part information outputted from the part recognition unit 12 may be managed by an image information database, or written as tags in the image data that have been already stored in the storage unit 15.

In the above explanation, after the part recognition is performed for each of the plural slice images included in one series, the part information of each slice is corrected by using the correlation of part information on plural slices. The advantage of performing part recognition through two stages is as follows. That is, part recognition processing can be started without waiting the input of all image data of one series to the server 2, and therefore, part recognition results can be obtained at a relatively high speed. Further, the part recognition result obtained for each slice is corrected based on the three-dimensional information of the object represented by the set of plural slice images, and therefore, major part recognition errors can be reduced. Thus, efficient and correct part recognition can be performed.

Here, the part recognition unit 12 shown in FIG. 2 performs part recognition processing on all inputted slice images. However, DICOM tags may be referred to before the part recognition processing is started, and the part recognition processing may be performed only on the slice images without information representing the imaging part ((0018, 0015): Body Part). This is because the part may be added in the imaging stage.

Alternatively, the part recognition unit 12 may perform the part recognition processing while thinning the continuously inputted slice images at predetermined slice intervals. In this case, the entire processing can be made faster. Furthermore, the part recognition unit 12 may perform the part recognition processing only on a predetermined range of the continuously inputted slice images. For example, when the subject of diagnosis is the abdomen of the object, the start region of the abdomen (or the mixture region of the chest and abdomen) is needed to be recognized. In this case, the part recognition processing may be omitted for the range that is obviously considered as the leg from the information representing the three-dimensional coordinates of the slice image (DICOM tag (0020, 0032): Image Position (Patient)), for example.

Further, when the parts of the body shown on the slices are tentatively determined at steps S3 and S4, parts may be recognized utilizing a machine learning method such as the neural network instead of using the score table.

When the neural network is utilized, the parts are tentatively determined in the following manner, for example. That is, as shown in FIG. 10, the feature quantities of the body part shown in the slice images (e.g., the feature quantities (A)-(C) explained at step S2) are inputted to the neural net. Then, the neural net is allowed to learn so that "1" is outputted for the part matching the part shown in the slice image and zero is outputted for other parts. For example, when the head is shown in the slice image, the output of "Head" is set to "1", and the outputs of "Neck", "Chest" and "Abdomen" are set to zero. Using thus learned neural network, the parts corresponding to the inputted feature quantities are acquired.

Next, the operation of the part segmentation processing unit 13 and the segmentation information addition processing unit 14 shown in FIG. 1 will be explained with reference to FIG. 11. The operation to be explained as below is executed by a CPU according to the medical image segmentation program stored in the storage unit 15. The medical image segmentation program allows the CPU to execute an operation of generating image data respectively representing two or more series of images based on the image data representing one series including plural axial images.

Figure 11:
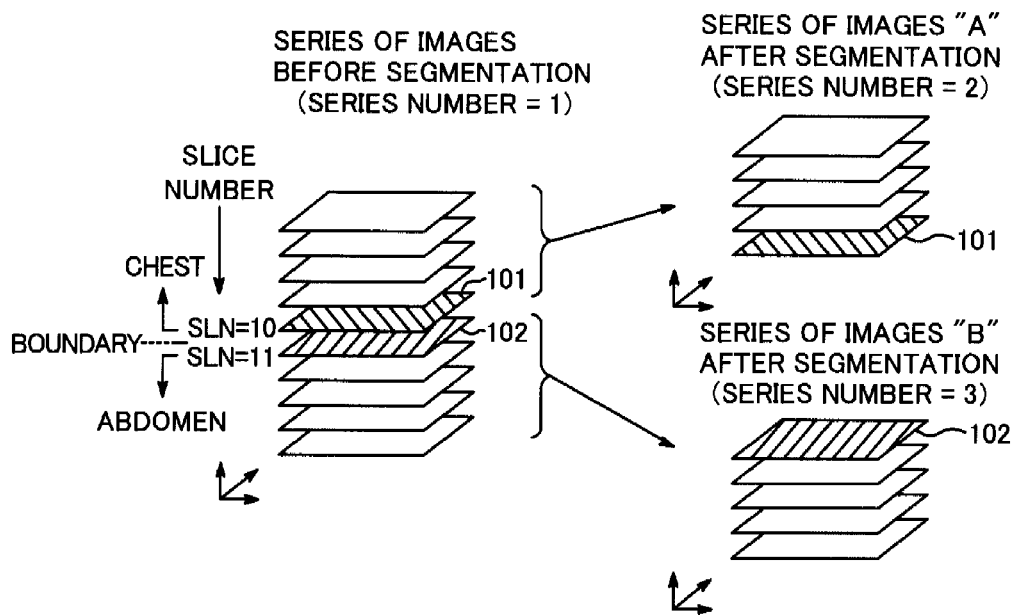
FIG. 11 is a diagram for explanation of an operation of a part segmentation processing unit and a segmentation information addition processing unit shown in FIG. 1.

The diagram on the left of FIG. 11 shows slice images included in a series before segmentation. In the series, the chest is shown in the slice images having slice number SLN of "10" and smaller, and the abdomen is shown in the slice images having slice number SLN of "11" and larger. Further, numbers indicating series (DICOM tag (0020, 0011): Series Number) are assigned to the respective slice images. In FIG. 11, the series number of the series before segmentation is "1".

When the series of images (series number=1) are acquired, the part segmentation processing unit 13 shown in FIG. 1 first detects a boundary between the parts based on the part information of the respective slice images and sets a position where the series is segmented based on the boundary. In FIG. 11, the part changes from the chest to the abdomen between the slice image 101 having slice number SLN of "10" and the slice image 102 having slice number SLN of "11". Accordingly, the part segmentation processing unit 13 determines that the region between the slice images 101 and 102 is a boundary between the parts and sets the region as a segmentation position.

Then, the part segmentation processing unit 13 changes the series number of the slice images, which have slice number SLN of "10" and smaller, from "1" to "2" to generate new series of images "A". Similarly, the part segmentation processing unit 13 changes the series number of the slice images, which have slice number SLN of "11" and larger, from "1" to "3", to generate new series of images "B". In this manner, segmented two series of images are generated.

Then, the segmentation information addition processing unit 14 shown in FIG. 1 creates tags indicating series numbers of adjacent series and adds information for identification of the adjacent series to the slice images at the ends of the series of images "A" and "B", that is, the slice images 101 and 102 in contact with the boundary. For example, the series number "3" indicating the series of images "B" is added as image supplementary information to the slice image 101 of the series of images "A", and the series number "2" indicating the series of images "A" is added as image supplementary information to the slice image 102 of the series of images "B".

Alternatively, the segmentation information addition processing unit 14 may add information with which the adjacent series can be directly searched (e.g., file names) as information for identification of adjacent series.

As described above, by adding information for identification of adjacent series to series of images showing a certain part, searching for images showing other parts concurrently imaged with respect to the same patient becomes easier.

Then, the segmentation information addition processing unit 14 creates DICOM tag (0020, 0052): Frame of Reference UID for the slice images 101 and 102, and adds numbers for unique identification of a coordinate system as reference as information representing the positional relationships with adjacent series. By adding the information representing such a common coordinate system to the series of images "A" and "B", the information ((0020, 0032): Image Position (Patient)) representing a three-dimensional coordinate system continuously held from the series of images before segmentation is determined to refer to the common coordinate system with respect to the respective series of images "A" and "B". As a result, the positional relationship between the series of images "A" and the series of images "B" (e.g., the vertical relationship) becomes clear according to the information representing the three-dimensional coordinate system.

Alternatively, the segmentation information addition processing unit 14 may add information (vector information) representing on which side of the x-axis, y-axis, or z-axis one series of images exist relative to the other series of images instead of generating the DICOM tag (0020, 0052): Frame of Reference UID).

When the series of images after segmentation are only two series, any information representing a positional relationship with adjacent series may not be added. This is because, as shown in FIG. 11, the positional relationship is determined by adding the series numbers of the adjacent series to the images 101 and 102 on ends of the series of images "A" and "B" after segmentation.

Referring to FIG. 1 again, for example, when a display command for the adjacent series is inputted by the user while the slice image included in the series of images "A" is displayed on the image display terminal 3, the adjacent image identification unit 16 searches for the image supplementary information of the series of images "A". When the series number (=3) of the adjacent series added to the slice image 101 (FIG. 11) is detected as a result, the adjacent image identification unit 16 causes the storage unit 16 to output the image data representing the series of images "B" having series number of "3" to the image display unit 3. Then, based on the DICOM tags (0020, 0052): Frame of Reference UID and (0020, 0032): Image Position (Patient) added to the slice image 101, the slice image 102 included in the series of images "B" is displayed next to the slice image 101 included in the series of images "A".

As explained above, according to the embodiment, since the information on the respective series are added to the respective series of images after segmentation, a slice image in the adjacent series can be easily searched for. Therefore, even when an original series is segmented in an inappropriate position and a desired slice image is determined not to be included in series of images during image interpretation, the slice image included in the related series of images can be easily displayed.

Next, a medical image segmentation apparatus according to the second embodiment of the present invention will be explained with reference to FIG. 12. The medical image segmentation apparatus according to the embodiment is different in the operation in the part segmentation processing unit 13 and the segmentation information addition processing unit 14 shown in FIG. 1 from that in the first embodiment. That is, in the embodiment, series segmentation is performed such that slice images partially overlap between two series of images. The rest of the configuration and operation is the same as that shown in FIG. 1.

Figure 12:
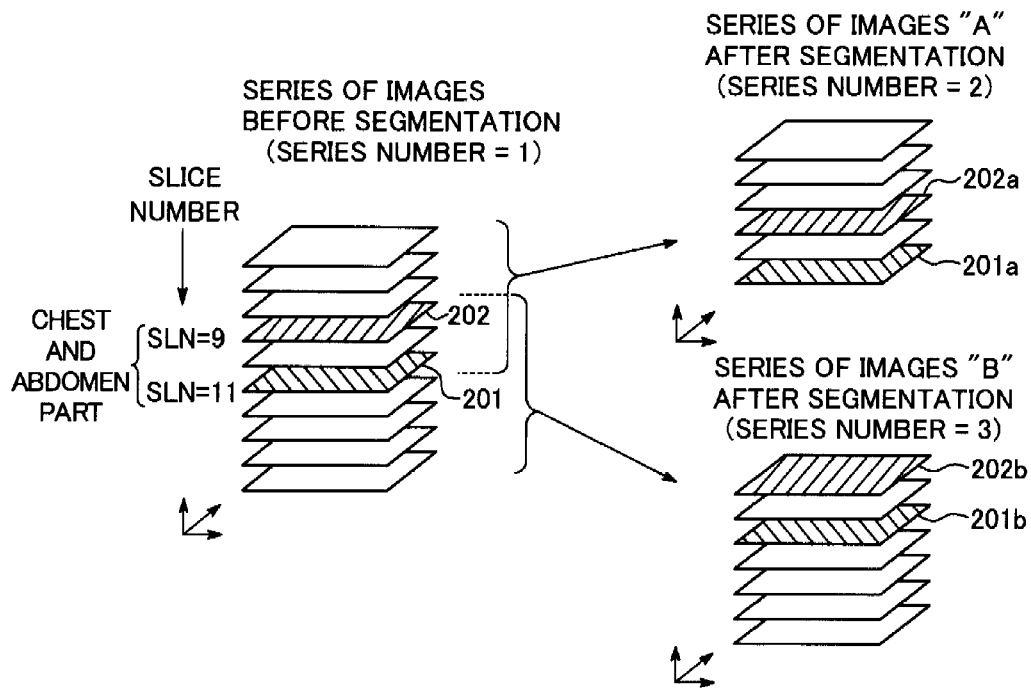
FIG. 12 is a diagram for explanation of an operation of a medical image segmentation apparatus according to the second embodiment of the present invention.

In the series of images before segmentation (series number=1) shown in FIG. 12, the part shown in the slice images having slice numbers SLN of "9-11" is determined to be the chest and abdomen part as a result of part recognition by the part recognition unit 12 in FIG. 1. Thus, in the case where the series of images before segmentation include slice images showing plural parts, the segmentation processing is performed in the following manner. That is, the part segmentation processing unit 13 changes the series number of the slice images, which have slice number SLN of "11" (the slice image 201 at the lower end of the chest and abdomen part) and smaller, from "1" to "2" to generate new series of images "A". Similarly, the part segmentation processing unit 13 changes the series number of the slice images, which have slice number SLN of "9" (the slice image 202 at the upper end of the chest and abdomen part) and larger, from "1" to "3" to generate new series of images "B".

Then, the segmentation information addition processing unit 14 shown in FIG. 1 adds information for identification of the adjacent series to the respective slice images 201a and 202b at the ends of the series of images "A" and "B" after segmentation. As the information for identification of the adjacent series, as is the case with the first embodiment, the series numbers of the adjacent series may be used or file names or the like may be used.

Further, the segmentation information addition processing unit 14 shown in FIG. 1 adds information representing the positional relationship with the adjacent series to the slice images 201a and 202b at the ends of the series of images "A" and "B" after segmentation. Furthermore, the segmentation information addition processing unit 14 may add information representing corresponding slice images to the ends of the slices overlapping in the series of images "A" and the series of images "B" after segmentation. In this case, for example, information representing the slice image 202b of the series of images "B" is added to the slice image 202a of the series of images "A", and information representing the slice image 201a of the series of images "A" is added to the slice image 201 of the series of images "B".

As the information representing the positional relationship with the adjacent series, as is the case with the first embodiment, DICOM tag (0020, 0052): Frame of Reference UID, i.e., information representing a common coordinate system may be used. In this case, from the information ((0020, 0032): Image Position (Patient)) representing three-dimensional coordinates continuously held by the respective series of images "A" and "B" from the series of images before segmentation, the positional relationship between both and corresponding slice images between both become clear.

The adjacent image identification unit 16 shown in FIG. 1, for example, searches for the image supplementary information of the series of images "A" when a display command for the adjacent series is inputted while the series of images "A" or "B" are displayed on the image display terminal 3, and thereby, detects the series number (=3) of the adjacent series added to the slice image 201a. Then, display of a series of slice images included in the series of images "B" is started from the slice image 201b (corresponding to the slice image 201a) based on the information representing the corresponding slice image.

As explained above, according to the second embodiment of the present invention, since the series segmentation is performed such that the slice images showing plural parts overlap in the series of images after segmentation, missing of parts can be prevented in both series of images after segmentation.

Further, according to the embodiment, to the corresponding slice images between series of images after segmentation, correlating information to each other is added, and thereby, the slice images of the adjacent series as the continuation of the series of images during interpretation can easily be searched for and displayed without duplication or loss.

As above, in the embodiment, the case where the slice images showing the plural parts (the chest and abdomen part in FIG. 12) are recognized by the part recognition unit 12 shown in FIG. 1 has been explained. However, as shown in FIG. 11, when a boundary can be set between two parts, series segmentation may be performed such that a predetermined range including the boundary overlap. For example, an area within ±Z cm from the boundary position set between SLN "10" and SLN "11" or an area of N slices (N is an integral number) from the boundary position is included in both the series of images "A" and the series of images "B" as an overlapping range.

Next, a medical image segmentation apparatus according to the third embodiment of the present invention will be explained with reference to FIG. 13. The medical image segmentation apparatus according to the embodiment is different in the operation in the part segmentation processing unit 13 and the segmentation information addition processing unit 14 shown in FIG. 1 from that in the first embodiment. That is, in the embodiment, volume data is configured based on the image data acquired by the modality 1 shown in FIG. 1. The rest of the configuration and operation is the same as that shown in FIG. 1.

Figure 13:
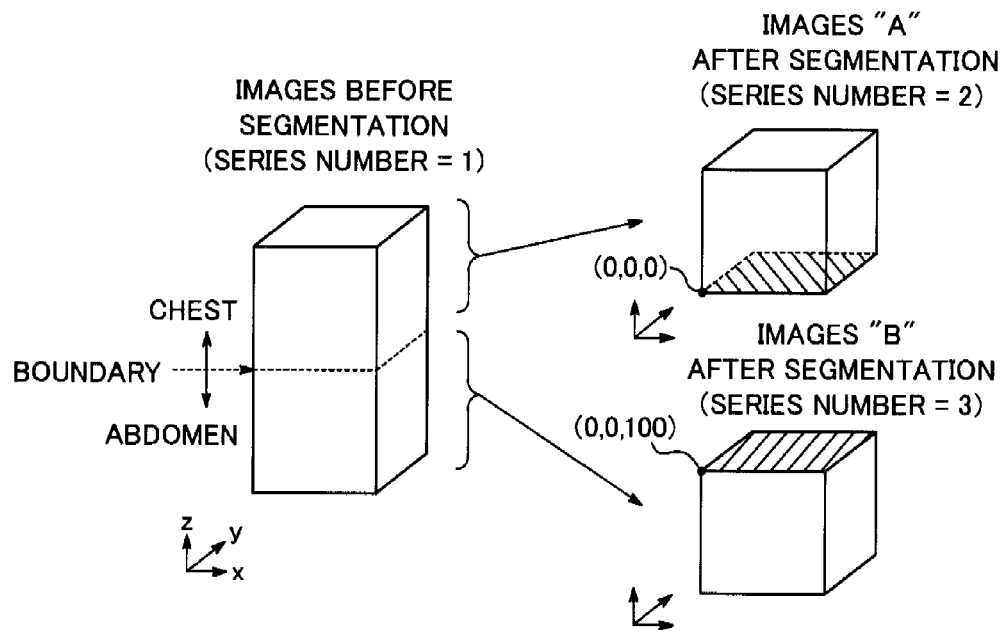
FIG. 13 is a diagram for explanation of an operation of a medical image segmentation apparatus according to the third embodiment of the present invention.

As shown in FIG. 13, the part segmentation processing unit 13 shown in FIG. 1 detects a surface (boundary surface) where the part changes in the z-axis direction based on the result of part recognition by the part recognition unit 12.

Then, the part segmentation processing unit 13 changes the series number from "1" to "2" with respect to volume data included in a range with a z-coordinate value larger than the z-coordinate of the boundary surface, and generates new volume data (images "A"). Similarly, the part segmentation processing unit 13 changes the series number from "1" to "3" with respect to volume data included in a range with a z-coordinate value smaller than the z-coordinate of the boundary surface, and generates new volume data (images "B").

Then, the segmentation information addition processing unit 14 shown in FIG. 1 adds information for identification of the adjacent images and the positional relationship with the adjacent images to the series of images "A" and "B" after segmentation. For example, to the images "A", information (0, 0, 0, 001) formed by adding identification number "001" to coordinates (0, 0, 0) contained in the boundary surface (z=0 surface) is added as image supplementary information. On the other hand, to the images "B", information (0, 0, 100, 001) formed by adding identification number "001" to coordinates (0, 0, 100) contained in the boundary surface (z=100 surface) is added as image supplementary information. From the identification number "001", the adjacency between the images "A" and the images "B" and the correspondence between the coordinates (0, 0, 0) within the images "A" and the coordinates (0, 0, 100) within the images "B" are identified.

Next, a medical image segmentation apparatus according to the fourth embodiment of the present invention will be explained with reference to FIG. 14. The medical image segmentation apparatus according to the embodiment is different in the operation in the part segmentation processing unit 13 and the segmentation information addition processing unit 14 shown in FIG. 1 from that in the first embodiment. That is, in the embodiment, segmentation into plural volume data is performed such that the volume data before segmentation partially overlap. The rest of the configuration and operation is the same as that shown in FIG. 1.

Figure 14:
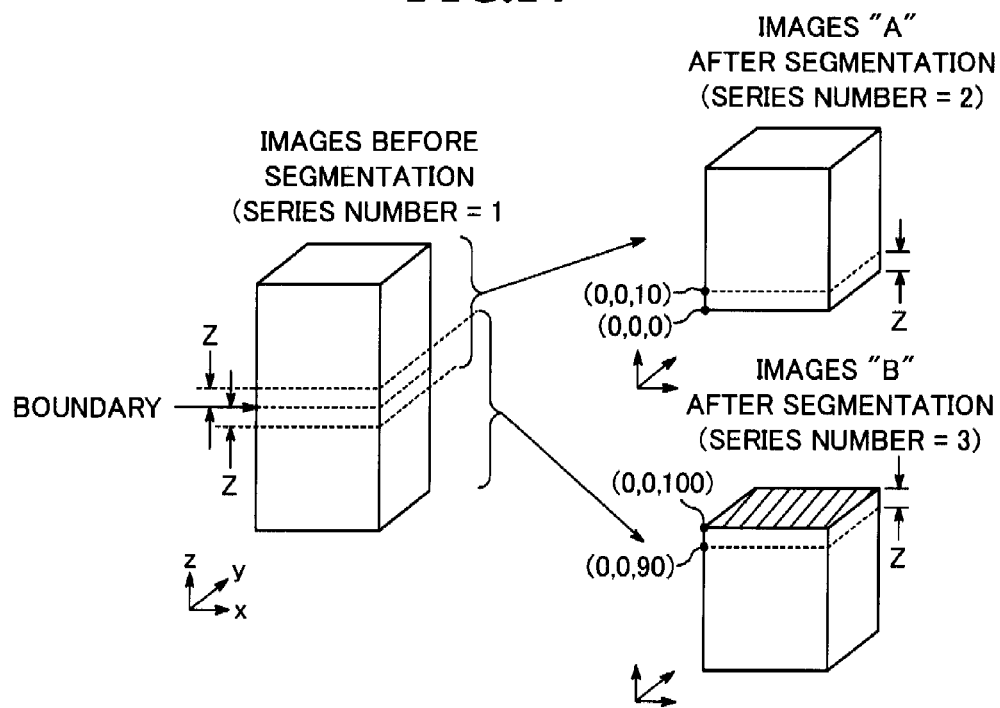
FIG. 14 is a diagram for explanation of an operation of a medical image segmentation apparatus according to the fourth embodiment of the present invention.

As shown in FIG. 14, the part segmentation processing unit 13 shown in FIG. 1 detects a surface (boundary surface) where the part changes in the z-axis direction based on the result of part recognition by the part recognition unit 12.

Then, the part segmentation processing unit 13 sets a range within ±Z cm from the boundary surface as an overlapping range in the volume data after segmentation. Then, the part segmentation processing unit 13 changes the series number from "1" to "2" with respect to volume data included in a range with a z-coordinate value larger than (the z-coordinate of the boundary surface −Z cm), and generates new volume data (images "A"). Similarly, the part segmentation processing unit 13 changes the series number from "1" to "3" with respect to volume data included in a range with a z-coordinate value smaller than (the z-coordinate of the boundary surface +Z cm), and generates new volume data (images "B").

Then, the segmentation information addition processing unit 14 shown in FIG. 1 adds information for identification of the adjacent images and the positional relationship with the adjacent images to the series of images "A" and "B" after segmentation. For example, to the images "A", information (0, 0, 0, 001) formed by adding identification number "001" to coordinates (0, 0, 0) and information (0, 0, 10, 002) formed by adding identification number "002" to coordinates (0, 0, 10) are added as image supplementary information. On the other hand, to the images "B", information (0, 0, 90, 001) formed by adding identification number "001" to coordinates (0, 0, 90) and information (0, 0, 100, 002) formed by adding identification number "002" to coordinates (0, 0, 100) are added as image supplementary information. Here, the coordinates (0, 0, 0) and (0, 0, 10) within the images "A" and the coordinates (0, 0, 100) and (0, 0, 90) within the images "B" are coordinates contained in the end surfaces of the overlapping range.

From the identification numbers "001" and "002", the adjacency between the images "A" and the images "B" can be identified. Further, the correspondence between the coordinates (0, 0, 0) within the images "A" and the coordinates (0, 0, 90) within the images "B" and the correspondence between the coordinates (0, 0, 10) within the images "A" and the coordinates (0, 0, 100) within the images "B" can be identified.

As above, in the embodiment, the case where a boundary can be set between two parts has been explained. However, in the case where the range showing two parts in one axial image (e.g., the chest and abdomen part) is recognized in advance, image segmentation may be performed to include the range in both of the images "A" and "B".

In the above-explained first to fourth embodiments, one series of axial images are segmented into two series, however, one series may be segmented into three or more series. In this case, information for identification of the adjacent series and the positional relationship with the adjacent series may be added to the respective segmented boundary surfaces and the respective end surfaces of overlapping ranges.

Next, a medical image segmentation apparatus according to the fifth embodiment of the present invention will be explained.

Figure 15:
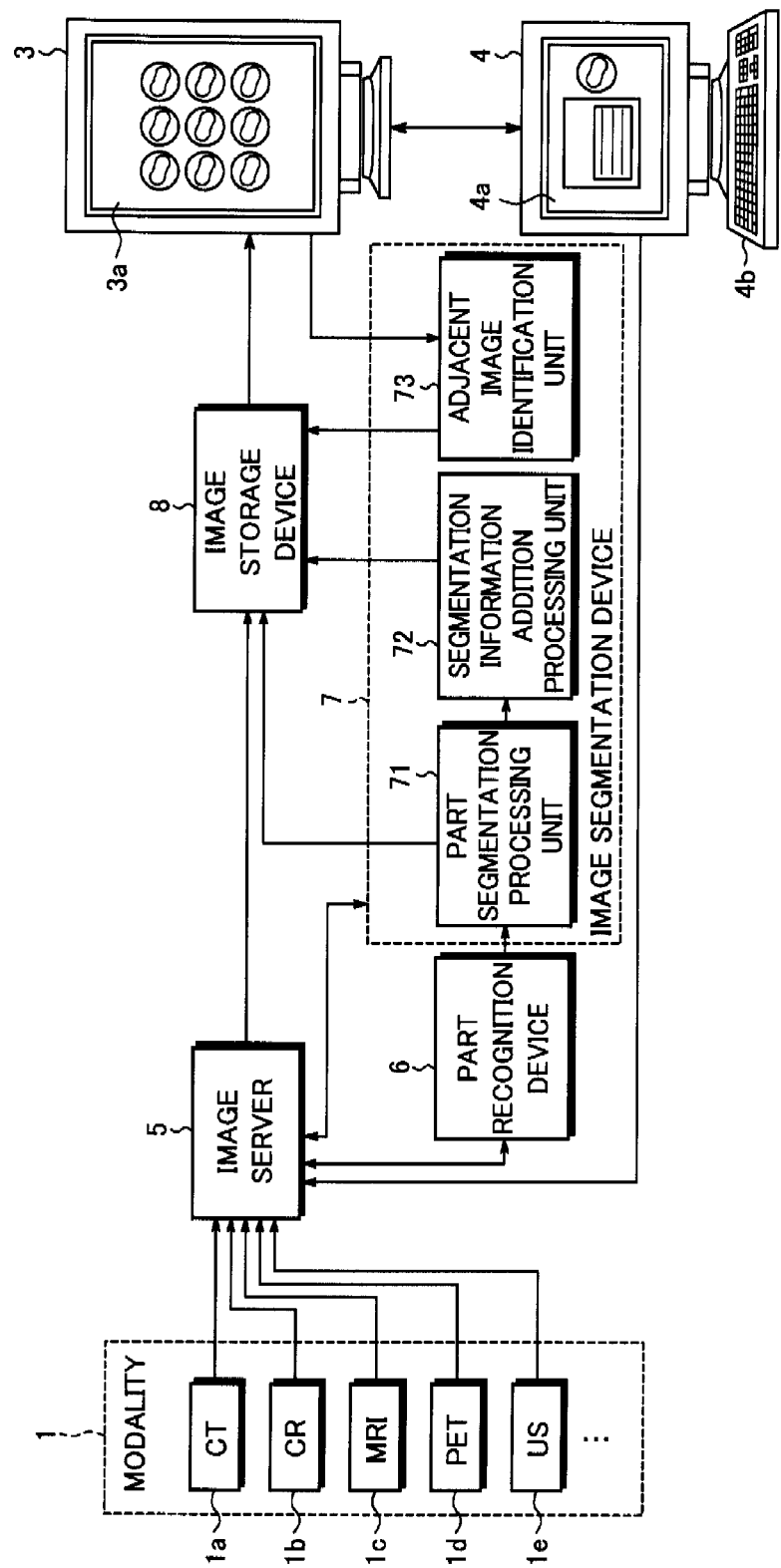
FIG. 15 shows a configuration of a medical image imaging system including a medical image segmentation apparatus according to the fifth embodiment of the present invention.

FIG. 15 is a block diagram showing a configuration of a medical image imaging system including the medical image segmentation apparatus according to the fifth embodiment. As shown in FIG. 15, this system includes an image server 5 in place of the image server 2 shown in FIG. 1, a part recognition device 6, an image segmentation device 7, and an image storage device 8. These devices 5-7 are compliant with the DICOM standard. The rest of the configuration is the same as that in the system shown in FIG. 1.

The image server 5 is a PACS server for storing and managing image data outputted from the modality 1. The image server 5 allows the image storage device 8 to store the image data inputted from the modality 1. Further, the image server 5 outputs the image data to the part recognition device 6 for part recognition when the image supplementary information of the image data does not include the information representing imaging part ((0018, 0015): Body Part). Furthermore, the image server 5 controls the image storage device 8 to output the image data stored in the image storage device 8 to the image display terminal 3 according to the request of the information image interpretation terminal 4.

The part recognition device 6 is a device for recognizing which part of the object is imaged in each axial image based on plural axial images represented by one series of image data and generating part information. The part recognition processing function and operation in the part recognition device 6 are the same as those in the part recognition unit 12 shown in FIGS. 1 and 2. Such a part recognition device 6 is configured by a personal computer (PC), for example.

The medical image segmentation device (hereinafter, also simply referred to as "image segmentation device") 7 includes a part segmentation processing unit 71, a segmentation information addition processing unit 72, and an adjacent image identification unit 73. The operations of these respective units are the same as those in the part segmentation processing unit 13, the segmentation information addition processing unit 14, and the adjacent image identification unit 16 shown in FIG. 1, respectively. Such an image segmentation device 7 is configured by a personal computer (PC) in which the above explained medical image segmentation program has been read, for example.

The image storage device 8 is, for example, a hard disk drive connected to the image server 5. Alternatively, as the recording medium, an MO, an MT, a RAM, a CD-ROM, a DVD-ROM, or the like may be used. In this case, a drive unit for driving those recording media is connected to the image server 5. Alternatively, an image storage unit may be built in the image server 5.

In the embodiment, the image segmentation device 7 is configured by a PC, and thereby, the image segmentation function can be easily provided in existing medical image imaging systems. Therefore, efficient image segmentation processing can be performed while existing equipment is used.

In the embodiment, the image segmentation device 7 outputs the image data after image segmentation and the image supplementary information thereof to the image storage device 8 to store them, however, the image data and the image supplementary information may be stored in a storage unit (e.g., a hard disk) built in the image segmentation device 7.

In the above explained first to fifth embodiments, the part recognition unit 12 (FIG. 1) and the part recognition device 6 (FIG. 15) perform part recognition processing on the image data directly inputted from the modality 1 to the image server 2 or 5. However, the image data that has been generated in the modality 1 and once stored in a recording medium may be loaded in the image server 2 or the part recognition device 6 for part recognition processing.

Figure 16:
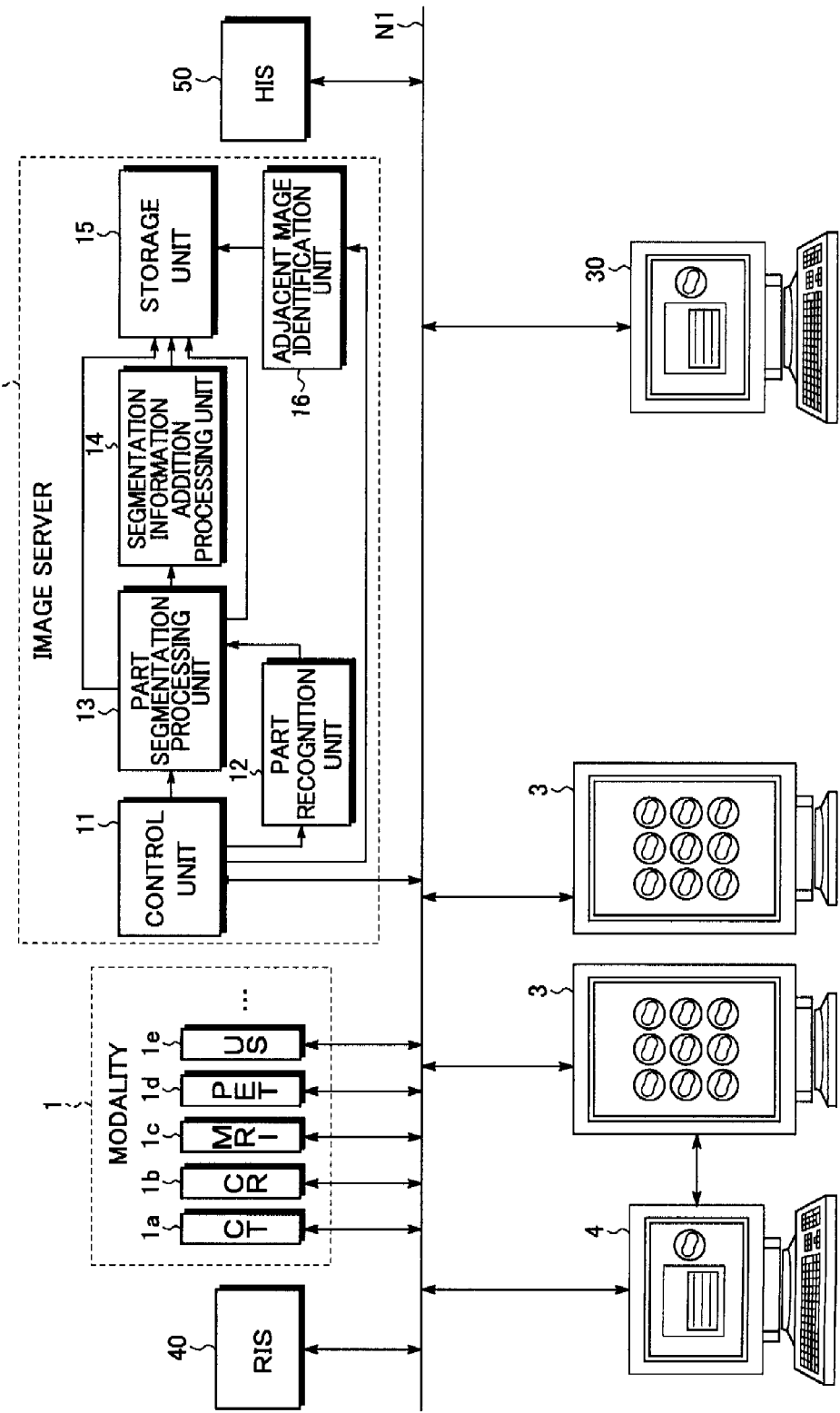
FIG. 16 shows another configuration example of the medical image imaging system including the medical image segmentation apparatus according to the first embodiment of the present invention.

Next, another configuration example of the medical image imaging system including the medical image segmentation apparatus according to the first to fifth embodiments of the present invention will be explained with reference to FIG. 16. As shown in FIG. 16, the modality 1, the image server 2, the image display terminal 3, and the image interpretation terminal 4 are connected to one another via network N1 such as a LAN (local area network) in the system. Alternatively, in place of the image server 2, the image server 5, the part recognition device 6, the image segmentation device 7, and the image storage device 8 shown in FIG. 15 may be connected to the network N1. Further, a terminal 30 installed in each department, an RIS (Radiology Information System) 40, and an HIS (Hospital Information System) 50 may be connected to the network N1.

As shown in FIG. 16, since the image server 2 (or the part segmentation device 7) having the medical image part segmentation function is connected to the network N1, series of images that have been appropriately segmented and series of images with which adjacent series are easily searched for can be utilized in various terminals (e.g., the image interpretation terminal 4 and each department terminal 30), and therefore, efficient image interpretation and medical diagnoses can be made.

INDUSTRIAL APPLICABILITY

The present invention is usable in a medical image segmentation apparatus for generating image data representing axial images segmented with respect to each part based on image data acquired by a medical imaging modality and representing axial images showing plural parts, and a medical image segmentation program to be used in the apparatus.

The invention claimed is:

1. A medical image segmentation apparatus for generating image data respectively representing plural series of images including at least first and second series of images based on image data representing one series of images including plural axial images, said apparatus comprising:
   image segmenting means for segmenting one series of images into a first series of images and a second series of images to thereby generate first image data representing the first series of images and second image data representing the second series of images; and
   segmentation information adding means for adding adjacent image information, which includes information for identification of the second series of images and information representing a positional relationship of the second series of images with the first series of images, to the first image data, and adding adjacent image information, which includes information for identification of the first series of images and information representing a positional relationship of the first series of images with the second series of images, to the second image data.

2. The medical image segmentation apparatus according to claim 1, further comprising:
   adjacent image identifying means for searching according to a signal externally inputted, when said first series of images are displayed on said display device connected to the medical image segmentation apparatus and receiving said first image data, for said second series of images based on the adjacent image information of said first series of images to cause said display device to display said second series of images.

3. The medical image segmentation apparatus according to claim 1, wherein said image segmenting means generates the first and second image data such that the first series of images and the second series of images overlap in a predetermined range in an axis direction.

4. The medical image segmentation apparatus according to claim 3, wherein said image segmenting means generates the first and second image data such that the first series of images and the second series of images overlap in a range in which plural parts are shown in one axial image.

5. The medical image segmentation apparatus according to claim 4, wherein said image segmenting means generates the first and second image data such that the first series of images and the second series of images overlap in a range in which (i) a head part and a neck part, (ii) a neck part and a chest, (iii) a chest and an abdomen, or (iv) an abdomen and a pelvis are shown in one axial image.

6. A medical image segmentation apparatus for generating image data respectively representing plural series of images including at least first and second series of images based on image data representing one series of images including plural axial images, said apparatus comprising:
   part recognizing means for recognizing parts shown in plural axial images represented by image data representing one series of images to generate part information; and
   image segmenting means for segmenting one series of images into a first series of images and a second series of images based on the part information generated by said part recognizing means to thereby generate first image data representing the first series of images and second image data representing the second series of images such that the first series of images and the second series of images overlap in a range in which plural parts are shown in one axial image.

7. A medical image segmentation program, embodied on a computer-readable medium, for generating image data respectively representing plural series of images including at least first and second series of images based on image data representing one series of images including plural axial images, said program actuating a CPU to execute the procedures of:
   (a) segmenting one series of images into a first series of images and a second series of images to thereby generate first image data representing the first series of images and second image data representing the second series of images; and
   (b) adding adjacent image information, which includes information for identification of the second series of images and information representing a positional relationship of the second series of images with the first series of images, to the first image data, and adding adjacent image information, which includes information for identification of the first series of images and information representing a positional relationship of the first series of images with the second series of images, to the second image data.

8. The medical image segmentation program according to claim 7, further actuating the CPU to execute the procedure of:
   searching according to a signal externally inputted, when said first series of images are displayed on said display device connected to a medical image segmentation apparatus and receiving said first image data, for said second series of images based on the adjacent image information of said first series of images to cause said display device to display said second series of images.

9. The medical image segmentation program according to claim 7, wherein procedure (a) includes generating the first and second image data such that the first series of images and the second series of images overlap in a predetermined range in an axis direction.

10. The medical image segmentation program according to claim 9, wherein procedure (a) includes generating the first and second image data such that the first series of images and the second series of images overlap in a range in which plural parts are shown in one axial image.

11. The medical image segmentation program according to claim 10, wherein step (b) includes generating the first and second image data such that the first series of images and the second series of images overlap in a range in which (i) a head part and a neck part, (ii) a neck part and a chest, (iii) a chest and an abdomen, or (iv) an abdomen and a pelvis are shown in one axial image.

12. A medical image segmentation program, embodied on a computer-readable medium, for generating image data respectively representing plural series of images including at least first and second series of images based on image data representing one series of images including plural axial images, said program actuating a CPU to execute the procedures of:
   (a) recognizing parts shown in plural axial images represented by image data representing one series of images to generate part information; and (b) segmenting one series of images into a first series of images and a second series of images based on the part information generated at procedure (a) to thereby generate first image data representing the first series of images and second image data representing the second series of images such that the first series of images and the second series of images overlap in a range in which plural parts are shown in one axial image.

* * * * *